United States Patent [19]

Sarda et al.

[11] Patent Number: 5,025,668

[45] Date of Patent: Jun. 25, 1991

[54] CELL FOR THE TRIAXIAL STRESS TESTING OF A ROCK SAMPLE AND A TESTING METHOD USING SUCH A CELL

[75] Inventors: Jean-Paul Sarda, Rueil-Malmaison; Guy Grard, Argenteuil, both of France

[73] Assignee: Institut Francais du Petrole, Rueil Malmaison, France

[21] Appl. No.: 374,150

[22] Filed: Jun. 30, 1989

[30] Foreign Application Priority Data

Jun. 30, 1988 [FR] France .................................. 88 08885

[51] Int. Cl.[5] .............................................. G01N 3/00
[52] U.S. Cl. ........................................................ 73/795
[58] Field of Search ................... 73/38, 794, 795, 819, 73/821, 825

[56] References Cited

U.S. PATENT DOCUMENTS

| | | | |
|---|---|---|---|
| 3,861,196 | 1/1975 | Domenighetti | 73/38 |
| 3,975,950 | 8/1976 | Erdei | 73/794 |
| 4,149,407 | 4/1979 | Strom et al. | 73/794 |
| 4,579,003 | 4/1986 | Riley | 73/794 |
| 4,599,891 | 7/1986 | Brauer et al. | 73/819 |

FOREIGN PATENT DOCUMENTS

| | | | |
|---|---|---|---|
| 0030488 | 3/1977 | Japan | 73/795 |
| 0151081 | 11/1961 | U.S.S.R. | 73/794 |

*Primary Examiner*—Robert Raevis
*Attorney, Agent, or Firm*—Antonelli, Terry, Stout & Kraus

[57] ABSTRACT

The present invention provides a cell for the triaxial stress testing of a rock sample, comprising a central body in which is placed a membrane enclosing said sample and exerting lateral stresses thereon, as well as a vertical pressure means acting on a section of the sample, said cell further comprising means for measuring the deformations of the sample related to the stresses which are applied thereto. The membrane has a central lateral opening in which the sample is introduced, a lateral external surface coming into contact with the body of the cell and a hollow internal volume forming a chamber providing confinement by means of a fluid introduced through an orifice.

10 Claims, 2 Drawing Sheets

CELL FOR THE TRIAXIAL STRESS TESTING OF A ROCK SAMPLE AND A TESTING METHOD USING SUCH A CELL

BACKGROUND OF THE INVENTION

1. Field of the Invention

The present invention relates to the field of stress testing carried out on a rock sample taken from a formation, such analyses making it possible to compare the properties and characteristics of the formation. It applies more particularly to a cell for the triaxial testing under stress of a sample and to the testing method using such a cell.

2. Description of the Prior Art

The devices used at the present time for the triaxial testing of rocks comprise a closed enclosure, in which the rock sample to be tested is introduced, this sample being then subjected to two types of stresses, a vertical stress exerted by a piston on the upper section of the rock and lateral stresses, exerted by a pressurized fluid in the enclosure via an impermeable resilient membrane.

In order to evaluate the deformation of the sample, stress gauges are bonded thereto and are connected by transmission wires to measuring apparatus situated outside the enclosure.

Such a device for the triaxial testing of samples has been used for a number of years in rock mechanics applications, but although the results of such measurements are satisfactory for the analyses developed, the use of the device is more problematic. Such a rock testing device is divulged particularly in the U.S. Pat. No. 3,975,950.

In fact, the preparation is long and often unsuitable. It is first of all necessary to fix the stress gauges to the sample, to introduce therein a tubular membrane of small thickness and to connect the gauges by wires passing through this membrane.

This preparatory step finished, the sample is placed in the enclosure of the testing cell and is held therein by the piston bearing on the upper edge of the sample. Then a confinement fluid is injected about the membrane until the desired confinement pressure is obtained. The membrane in contact with this pressurized fluid then transmits lateral stresses to the rock.

The progressive force exerted by the piston is transmitted through the rock in the form of increasing deformations detected by the stress gauges, the stress exerted by the piston being able to go up to rupture of the structure of the sample.

This type of installation for triaxial testing has the manifest drawbacks of a long and inconvenient setting up phase. It is not always simple to empty the cell in order to withdraw the fractured sample and to uncouple the electric connections when the liquid may still be present on the tubular membrane. In addition, the problems are even more numerous when the rock is appreciably saturated with water for, in this case, fixing of the stress gauges becomes excessively difficult, as well as the passage of the connecting wires through the membrane. Finally, a major drawback of such a device is that it detects the pinpoint deformations at the level of each stress gauge, whereas it is important to be able to detect an overall displacement of the sample. Such an overall displacement announces a more or less pronounced anomaly of the test, and forms the only possible measurement in the case of rupture of the sample, the stress gauges then becoming inactive because they are pinpoint.

The information concerning the deformation at the time of rupture is no longer available, in the case of stress gauges, whereas it plays an essential role in the analysis of the mechanism of rupture of the material.

SUMMARY OF THE INVENTION

The purpose of the present invention is then to overcome the drawbacks of conventional triaxial testing devices of the prior art, by considerably simplifying, by means of a new structure, the operations for installing the sample and the associated measurement devices.

It also makes it possible to measure jointly the pinpoint deformations at the level of the stress gauges and the displacements of the sample introduced into the enclosure, under the effect of the forces applied, this displacement measurement being essential in the procedure of analysis beyond the rupture.

The basic idea of the present invention is to use a cell comprising a membrane in which the sample is introduced. It has a hollow internal volume of "inner tube" type exerting a homogeneous pressure over the whole surface of the sample. This membrane contains a fluid injection input which exerts the lateral stresses on the rock at a given pressure.

The object of the present invention is then to provide a cell for the triaxial stress testing of a rock sample, comprising a central body exerting lateral stresses on said sample as well as a means of exerting a vertical pressure on a section of the sample, a membrane enclosing said sample, said cell further comprising means for measuring the deformations of the sample related to the stresses which are applied thereto, wherein said membrane introduced into the central body comes into contact at an external surface with said body and has a central longitudinal opening in which the sample is introduced, said sample being in contact with an inner surface of the longitudinal opening of the membrane and said membrane comprising a hollow internal volume forming a chamber for confinement by means of a fluid introduced through an orifice.

By using an appropriate shape of the membrane having a hollow internal volume in which a pressurized fluid is injected, the setting up and emptying problems existing in prior art devices are overcome.

According to an advantageous characteristic of the invention, the means for measuring the deformations comprise members measuring the displacement of the sample.

These displacement measurement members comprise, in a preferred embodiment, at least two rods each of which comes into contact at a first end with the surface of the sample and at a second end with a displacement sensor, said rods passing through the chamber for confinement of said membrane through a fluid tight duct.

The use of rods in contact with the surface of the sample and transmitting the displacement movements to the sensors, makes it possible to associate, with the usual analysis of stress gauges, the measurements related to the lateral displacement of the sample as a whole, these displacement measurements being the only measurements available after rupture of the sample.

In a particular embodiment, the vertical pressure means comprise a cylindrical piston having a cross section substantially less than the central opening of the membrane and pierced with holes. The stress gauges are advantageously placed against the surface of the sample and connected to measurement apparatus by connecting wires passing through the holes formed in the piston.

Positioning of the stress gauges is all the easier with the present invention, since it is no longer necessary to pass the connecting wires through the membrane, they can be disposed side by side between the internal wall of the membrane and the sample as far as its upper part, then passed through the piston for connection with measurement apparatus external to the enclosure.

Thus, with the present invention, the difficulties of connecting the stress gauges through the membrane are overcome.

In a preferred embodiment of the invention, the displacement sensors rest on stirrup pieces mounted on the external surface of the body of the cell.

Advantageously, the membrane of the invention rests in the body of the cell on a base, at least one part of which is engaged in the central opening while providing circumferential sealing.

In accordance with a particular characteristic of the invention, the displacement measurement members are situated in the same horizontal plane, substantially in the middle of the sample in its longitudinal direction.

The present invention also relates to a method of triaxial stress testing of a rock sample using a cell such as described above, in which:
- a membrane is introduced into the body of the cell so that the walls of said membrane bear against said body,
- a sample to be tested is placed in the center of said membrane, so that the walls of the sample are in contact with said membrane,
- a fluid is injected into the confinement chamber for exerting an homogeneous lateral confinement pressure over the whole surface of the sample,
- the displacement sensors mounted on the stirrup pieces are set to a zero position,
- a vertical pressure is exerted by the action of the piston, and
- the displacement of said sample is measured by the sensors.

The triaxial testing method of the present invention considerably simplifies the phase preparatory to the measurement particularly in so far as the positioning of the lateral stresses is concerned.

BRIEF DESCRIPTION OF THE DRAWINGS

A particular embodiment of the invention is hereinafter described in greater detail to show the essential features and advantages of the invention, it however being understood that this embodiment is chosen by way of example and is in no wise limitative. The description is illustrated by the following drawings in which.

DESCRIPTION OF THE PREFERRED EMBODIMENTS

Figure 1:
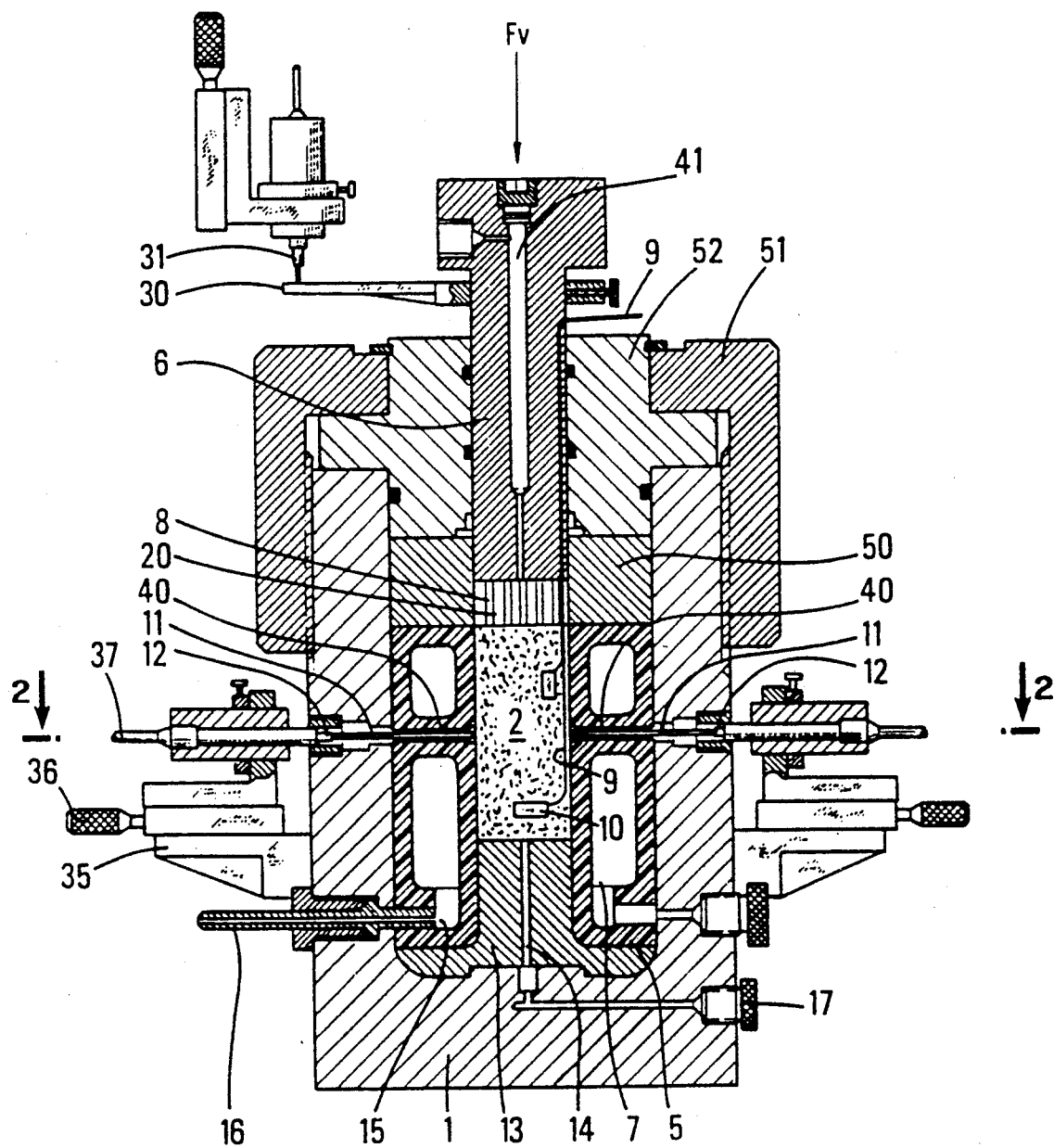
FIG. 1 shows a triaxial testing cell in accordance with the present invention in vertical section.

FIG. 1 shows a cell for the triaxial stress testing of a rock sample 2.

This cell comprises a body 1 having a generally cylindrical shape which could possibly be of square or rectangular section without modifying the scope of the present invention) whose central portion forms the triaxial sample testing enclosure.

At the bottom of the internal enclosure of body 1 of the cell is formed a base 13 on which rests a membrane 5 loaded so as to exert lateral pressures on the sample to be tested.

This membrane 5 has a central longitudinal opening in which sample 2 is introduced. Its external surface bears against the internal surface of body 1 of the cell. In a preferred embodiment, the central opening will be of cylindrical shape and the external section of the membrane will be circular.

The shape of the membrane may however be readily transformed without however modifying the characteristics of the invention in the case where the sample taken is not a cylindrical core sample or where the enclosure of the body of the cell is not of circular section.

Membrane 5 bears over the whole of its external surface against the body of cell 1 and at its lower part against base 13. The form of base 13 is designed so that a portion is engaged in the central opening of membrane 5 for providing stable positioning of said membrane at the bottom of the enclosure while prohibiting any lateral movement and for providing optimum circumferential sealing at the level of the support surface of the sample.

Membrane 5 comprises a hollow internal volume giving it a "inner tube" type configuration. This hollow internal volume 7 is filled with a confinement fluid injected through an introduction orifice 15, so as to form a confinement chamber whose pressure will increase by the injection of fluid and which will then exert increasing lateral stresses on the sample.

The introduction orifice 15 is formed on the low part of membrane 5 and is placed in relation with an inlet duct 16 passing through body 1 and connected to injection means which are usually used (not shown).

The injection pressure of the fluid through duct 16 is of the order of 100 bars, but conclusive tests have shown that such a device can be used up to pressures of about 450 bars.

The membrane will be made from a relatively rigid resilient material, such as butyl and the fluid used in the confinement chamber may be water, oil or even mercury.

Sample 2 introduced into the central part of the membrane will have been taken from the formation so as to have a diameter slightly less than the diameter of the central portion so as to facilitate its introduction. When the pressure in chamber 7 increases through the introduction of fluid, the membrane will be deformed slightly and will then provide a contact on the sample so as to exert an homogeneous pressure over the whole of its surface. Sample 2 placed in the cell is subjected to two types of stresses: a first vertical stress exerted by a pressure of piston type and lateral stresses provided by pressurizing the confinement chamber. These stresses transmit to the sample deformations whose variations it is desired to measure.

Two means will be used for measuring these deformations: stress gauges usually used in this field and displacement measurement members.

In a preferred embodiment, the triaxial testing cell comprises a vertical pressure means formed by a piston 6. This piston 6 is cylindrical in shape and has a cross section slightly less than the central opening of the membrane so as to be able to exert a vertical pressure force on the sample.

Piston 6 comprises on its low part a bearing piece 8 which provides permanent contact with the sample. This bearing piece 8 is pierced with holes 20 which open into a hollow volume of the body of piston 6.

The purpose of these holes 20 is to remove towards the body of the piston the water which may be present in the sample, when a pressure is exerted.

The vertical pressure force, shown in FIG. 1 by a reference arrow $F_V$, may be exerted by any pressure means which are usually used in the field considered, in which tensimeters are generally associated for measuring the pressure considered.

Using the present invention, it is further proposed to measure, by means of a displacement sensor 31 cooperating with a plate 30 fast with the body of the piston, the variations of the vertical displacement transmitted by the sample.

The triaxial testing cell comprises two other types of deformation measurement means. First of all, stress gauges 10 usually used in devices of the prior art. These stress gauges are fixed to the sample before being introduced into the cell. Four gauges are generally used, two placed in a vertical direction and the other two in a horizontal direction.

After introducing the sample into the membrane, the connecting wires 9 connected to these gauges 10 are guided to the outside of the cell by passing through the bearing piece 8 of the piston at the level of holes 20. These holes provide therefore both the function of removing the water in suspense and the function of allowing the connecting wires to pass outside the membrane.

The second means for measuring the deformations exerted on the sample is formed by members measuring the lateral displacements of the sample. They are clearly visible in FIG. 2, to which reference will be made in association with FIG. 1 for the following description.

The measurement of the lateral displacement of the sample, namely the increase in its diameter under the effect of the pressure exerted (phenomenon generally called barrel effect) is provided by rods 11 which transmit the compression of the sample to the displacement sensors 12.

Figure 2:
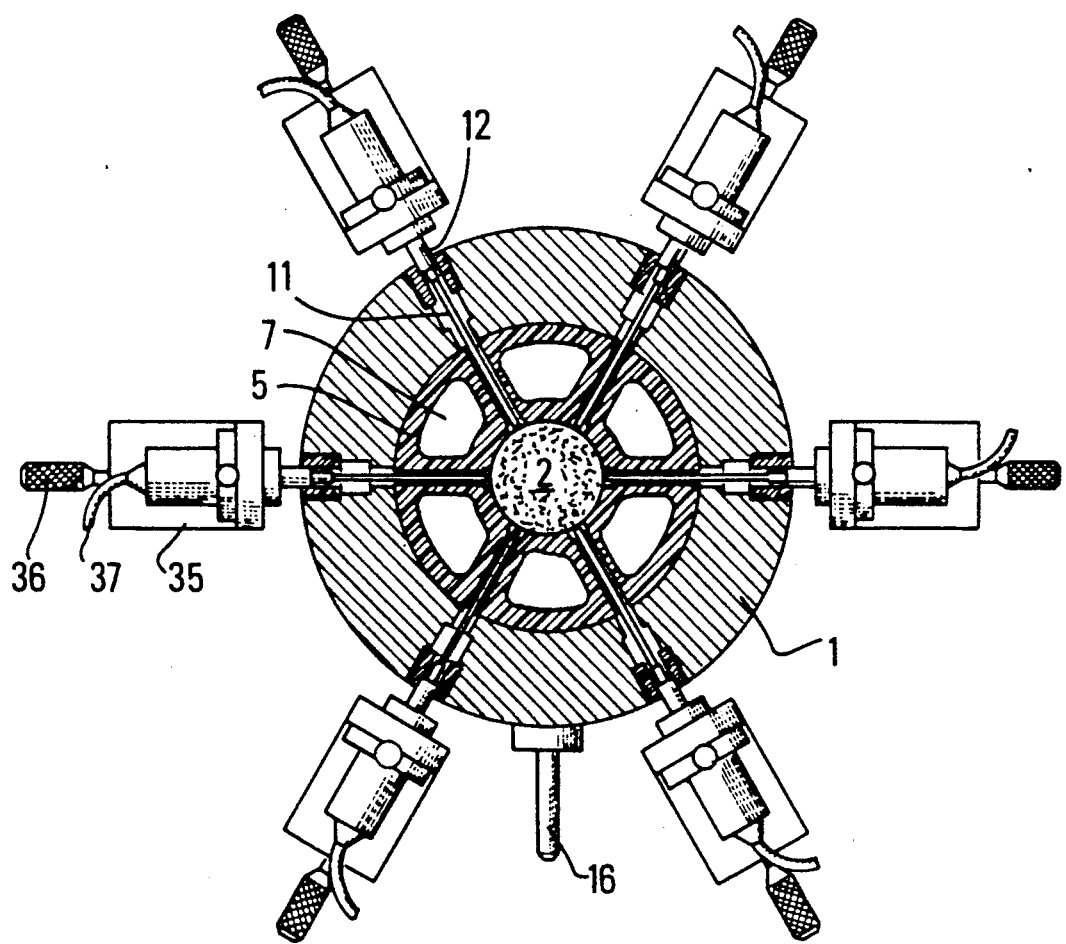
FIG. 2 shows the cell in horizontal section at the level of the displacement sensors.

FIG. 2 shows the use of six displacement sensors spaced evenly apart about the membrane. It will be readily understood that the present invention also applies in the case where only four sensors are used.

In a preferred embodiment, these sensors are situated in the same horizontal plane substantially in the middle of sample 2 in its longitudinal direction.

Rods 11 are formed by fine elements in contact at one of their ends with the surface of sample 2 and at their other end in contact with the displacement sensors 12.

These rods pass through membrane 5, particularly at the level of its confinement chamber 7, through an internal duct 40 sealed to the injected fluid. These ducts 40 allow the sensors to come into contact with the sample, while maintaining the confinement chamber closed.

The displacement sensors 12 are engaged in openings formed in the body of the cell.

They rest on stirrup pieces 35 fixed to the wall of the body of the cell. These sensors comprise adjustment means 36, such as micrometric screws, by which they can be moved slightly on the stirrup pieces and be positioned at a point forming reference 0 of the measurement. These sensors may be formed of telescopic tubes with extension return means whose displacement with respect to each other is measured so as to derive the distance travelled.

The sensors are connected to central analysis means (not shown) by cables 37.

The overall displacement of the sample measured by such means makes it possible to analyse information which was not available from the stress gauge measurements. Such overall displacement of the sample also makes it possible to detect a more or less pronounced anomaly of the test, such for example as the effect of parallelism of the loading bases, a centering defect of the charge or of the parallelism of the sections of the sample, heterogeneity of the deformation properties of the material.

The displacement measurement by sensors 12 plays an essential role in the case of rupture of the sample, for often the stress gauges are then no longer usable, although the deformation information in this phase plays an essential role in the analysis of the mechanism of rupture of the material.

To obtain the best possible analysis, sensors 12 associated with rods 11 are disposed in a horizontal plane at the level of the membrane substantially close to the center of the length of the sample when the latter is introduced into the cell.

Since tests on porous water saturated samples is particularly interesting, the cell further comprises a liquid inlet 41 passing through the piston and injecting water into the sample. When the water has diffused throughout the rock and when the latter is saturated, the water flows away through a duct 14 formed in base 13 towards the outside of the cell through an outlet 17.

The cell also comprises a blocking piece 50 placed above the membrane which guides the piston in translation during positioning thereof.

Means for closing enclosure 51,52 are in the form of a part screwed to body 1.

The method of using such a cell is considerably simplified with respect to prior art devices.

With the closure means of the enclosure withdrawn and the confinement pressure inside the membrane zero, the sample is introduced into the center of this membrane, then the piston is positioned on the upper surface of the assembly.

Then the desired confinement pressure is established in the chamber of the membrane.

The zero of the displacement sensors is set by means of the micrometric screws at the level of each stirrup piece.

A vertical pressure force is exerted through the piston and the deformations obtained are recorded by the stress gauges and the displacement sensors.

The present invention overcomes the problems of prior art devices, particularly by doing away with the emptying operation between measurements and also makes it possible to obtain information concerning the sample which was not available after rupture of the rock.

The invention is not limited by the features which have been more specifically described, or by the details of the particular embodiment chosen for illustrating the invention.

All sorts of variations may be made to the particular embodiment which has been described by way of example and to its component elements, without departing from the scope of the invention.

The invention thus covers all the means forming technical equivalents of the means described, as well as combinations thereof.

What is claimed is:

1. A cell for the triaxial stress testing of a rock sample, comprising a central body including a means for exerting lateral stresses on said sample and a means for exerting a vertical pressure on a section of the sample, said means for exerting lateral stresses comprising a membrane enclosing said sample, said cell further comprising means for measuring the deformations of the sample related to the stresses which are applied thereto, wherein said membrane positioned within the central body has an external surface that comes into contact with said body and has a central longitudinal opening in which the sample is positioned, said sample being in contact with an inner surface of the membrane which defines the longitudinal opening and said membrane comprising a resilient member having a hollow internal volume forming a chamber for confinement of a fluid introduced into the chamber through an orifice connected to said membrane.

2. The triaxial testing cell as claimed in claim 1, wherein said means for measuring the deformations comprise members measuring the displacement of the sample.

3. The triaxial testing cell as claimed in claim 2, wherein said displacement measurement members comprise at least two rods each of which comes into contact at a first end with a surface of the sample and at a second end with a displacement sensor, said rods passing through a fluid tight duct provided by a wall portion of the membrane forming the chamber for confinement of said fluid.

4. The triaxial testing cell as claimed in claim 3, wherein the vertical pressure means comprise a cylindrical piston having a cross section substantially less than the central opening of the membrane and a surface bearing on the sample which is pierced with holes.

5. The triaxial testing cell as claimed in claim 4, wherein said measuring means further comprise stress gauges placed against the surface of the sample and connected to a measurement apparatus by connecting wires passing through the holes formed in the piston.

6. The triaxial testing cell as claimed in claim 3, wherein the displacement sensors rest on stirrup elements mounted on an external surface of the body of the cell.

7. The triaxial testing cell as claimed in claim 2, wherein said membrane rests in the body of the cell on a base, at least part of said base being engaged in a lower portion of the central opening and providing circumferential sealing about the membrane.

8. The triaxial testing cell as claimed in claim 2, wherein said displacement measurement members are situated in the same horizontal plane, substantially in the middle of the sample in its longitudinal direction.

9. A method for the triaxial stress testing of a rock sample using a triaxial testing cell, wherein:
   a membrane is positioned within a body of the cell so that external walls of said membrane bear against said body,
   a sample to be tested is placed in a central opening of said membrane, so that walls of the sample are in contact with said membrane,
   a fluid is injected into a confinement chamber defined within said membrane for exerting a homogeneous lateral confinement pressure over a whole lateral surface of the sample,
   displacement sensors mounted on stirrup elements of the cell are set to a zero position,
   a vertical pressure is exerted on the sample by the action of means for exerting a vertical pressure on a section of the sample within the central opening, and
   displacement of said sample is measured by the sensors.

10. The method as claimed in claim 9, wherein said means includes a piston and, prior to introduction of the membrane, stress gauges are fixed against the sample and the connecting wires are passed through holes formed in the piston.

* * * * *